US005625105A

United States Patent [19]

Lin et al.

[11] Patent Number: 5,625,105
[45] Date of Patent: Apr. 29, 1997

[54] PRODUCTION OF VINYLIDENE OLEFINS

[75] Inventors: Kaung-Far Lin, Baton Rouge; Carroll W. Lanier, Baker, both of La.

[73] Assignee: Amoco Corporation, Chicago, Ill.

[21] Appl. No.: 596,848

[22] Filed: Feb. 5, 1996

[51] Int. Cl.$^6$ .................................................. C07C 2/26
[52] U.S. Cl. ............................................. 585/511; 585/512
[58] Field of Search .................................. 585/511, 512

[56] References Cited

U.S. PATENT DOCUMENTS

| | | | |
|---|---|---|---|
| 4,155,946 | 5/1979 | Sato et al. | 585/513 |
| 4,709,112 | 11/1987 | Sato et al. | 585/513 |
| 4,795,851 | 1/1989 | Frame et al. | 585/512 |
| 4,973,788 | 11/1990 | Lin et al. | 585/511 |
| 5,124,465 | 6/1992 | Allen et al. | 556/190 |
| 5,516,958 | 5/1996 | Schaerfl, Jr. et al. | 585/511 |

*Primary Examiner*—Jacqueline V. Howard
*Attorney, Agent, or Firm*—Joseph DiSalvo; Stephen L. Hensley

[57] ABSTRACT

Vinylidene olefin can be formed in good yield in much shorter reaction periods than found critical heretofore. The process involves dimerizing vinyl olefin with at least one trialkylaluminum compound as the sole catalyst component charged to the reaction vessel. These materials are charged to the reactor so that it contains in the range of 0.001 to 0.05 mol of trialkylaluminum per mol of the initial vinyl olefin. The reaction is performed at a temperature in the range of over 140° C. and below 172° C. for a period of time in the range of 1 to 24 hours sufficient to convert at least 10% by weight of the initial vinyl olefin to a different product with at least 80 wt % vinylidene dimer selectivity.

21 Claims, No Drawings

PRODUCTION OF VINYLIDENE OLEFINS

TECHNICAL FIELD

This invention relates to a process enabling vinylidene olefins to be produced in good yields in relatively short reaction periods.

BACKGROUND

Vinylidene olefin, which are branched monoolefins having the structure $(R^1)(R^2)C=CH_2$ where $R^1$ and $R^2$ are alkyl groups, are of commercial importance as raw materials for use in producing-double tailed oxo alcohols and other functionalized derivatives, used in the manufacture of detergents, surfactants, specialty agricultural chemicals, and fuel or lubricant additives. Vinylidene olefins can be produced by dimerizing vinyl olefins.

U.S. Pat. No. 4,155,946 to Sato, Noguchi and Yasui discloses a process for dimerizing lower $\alpha$-olefins in which the catalyst system is formed from (1) a trialkylaluminum compound, (2) a salt or complex of nickel, (3) a trivalent phosphorus compound selected from specified groups, and (4) a halogenated phenol.

U.S. Pat. No. 4,709,112 to Sato, Ikimi, Tojima and Takahashi describes a process for dimerizing lower $\alpha$-olefins which uses a catalyst system formed from (1) a trialkylaluminum compound, (2) an organic salt or complex of nickel, (3) a trivalent phosphorus compound selected from specified groups, (4) a fluorinated isopropanol, and (5) a catalyst co-activator selected from specified types of halogenated compounds.

U.S. Pat. No. 4,973,788 to Lin, Nelson and Lanier describes a process for dimerizing a vinyl olefin monomer at a selectivity of at least 85 mol percent. This is accomplished by use of a catalyst which consists essentially of 0.001–0.04 mols of trialkylaluminum per mol of vinyl olefin, and conducting the reaction at a temperature in the range of about 100°–140° C. for a time sufficient to convert at least 80 mol percent of the initial vinyl olefin to a different product. The reaction rate under these conditions is quite slow, and thus a long reaction time is required. For example it is pointed out that the time required for 90 percent conversion at 120° C. with 0.043 mols of aluminum alkyl catalyst per mol of initial vinyl olefin is about 94 hours, and that with 0.017 mols of the catalyst per mol of initial vinyl olefin the time required at 120° C. is about 192 hours. It is also shown in the patent that although the reaction is faster at 172° C. compared to 120° C., the selectivity to vinylidene dimer is only 71 percent compared to 90 percent with the same catalyst concentration but at 120° C.

In the presence of aluminum alkyl, vinyl olefins are dimerized to vinylidene olefins via the Markovnikov route. However a competing reaction which adversely affects yield of vinylidene olefin or the purity thereof is the dimerization to deep internal olefin dimer via the anti-Markovnikov route. Another undesirable competing reaction which normally tends to occur at dimerization temperatures is the isomerization of vinyl olefin to internal isomer olefin via aluminum hydride route or by other known mechanisms. Such internal olefin formation adversely affects the dimer selectivity. It would be extremely desirable to suppress these competing reactions and be able to achieve high selectivity to vinylidene dimer in substantially shorter reaction periods than required in the process of U.S. Pat. No. 4,973,788 and without need for multicomponent catalyst systems such as described in U.S. Pat. Nos. 4,155,946 and 4,709,112.

The present invention has accomplished this goal.

THE INVENTION

In accordance with this invention, it has been found that it is possible to achieve high selectivity to vinylidene dimer in substantially shorter reaction periods than required in the process of U.S. Pat. No. 4,973,788 using a trialkylaluminum compound as the sole catalyst component charged to the reaction vessel. This can be accomplished by dimerizing vinyl olefin with at least one trialkylaluminum compound as the catalyst in a ratio in the range of 0.001 to 0.05 mol of trialkylaluminum per mol of the initial vinyl olefin at a temperature in the range of over 140° C. and below 172° C. for a period of time in the range of 1 to 24 hours sufficient to convert at least 10% by weight of the initial vinyl olefin to a different product with at least 80 wt % vinylidene dimer selectivity. In a preferred embodiment, the process is conducted for a period of time in the range of 6 to 24 hours sufficient to convert at least 60% by weight of the initial vinyl olefin to a different product with at least 80 wt % vinylidene dimer selectivity.

The use of the above reaction conditions suppresses isomerization to internal olefins and enhances vinylidene dimer selectivity.

Another feature of the process of this invention is that it takes advantage of the exothermic nature of the olefin dimerization reaction. For example, the heat of reaction is about 20 Kcal per g mol of dimer formed. Thus by operating in the above temperature range, external energy requirements and costs can be kept to a minimum.

There are three preferred general modes in which the process of this invention can be carried out. One such mode involves use of a single reactor commonly referred to as a "stirred pot reactor" in which the reaction is conducted with agitation on a batch basis. In another such mode the reactor comprises at least two closed vessels in which the reaction is conducted with agitation and continuous feed, the vessels being connected in series such that the feed rate to the first vessel, and the discharge rates from each vessel to the ensuing vessel, where there is an ensuing vessel, are substantially equal to each other. The third mode utilizes a single continuous elongated reactor in which the reaction is conducted with agitation on a continuous basis. When conducting the first or third of these modes it is particularly preferred to perform the reaction such that during at least 50 percent of the time that the reaction mixture is at a temperature above about 110° C.: (a) the vapor space in the reactor is in the range of 0 to 40 percent (more preferably in the range of up to 30 percent, still more preferably in the range of no more than 20 percent, and most preferably in the range of no more than 10 percent) of the total interior free space of the reactor, and (b) the remainder of the free space in the reactor contains an inert atmosphere. In the case of the second above mode of operation, the reaction is most preferably conducted such that during at least 50 percent of the time that the reaction mixture is at a temperature above about 110° C. in one or more of the vessels: (a) the vapor space in such vessels is in accordance with the ranges given above, e.g., the total vapor space is in the range of 0 to 40 percent but most preferably no more than 10 percent of the total interior free space of the vessels, and (b) the remainder of the free space in the vessels contains an inert atmosphere.

In a preferred embodiment the process is conducted whereby the relationship among vinyl olefin conversion, reaction time and catalyst concentration is in accordance with the expression:

$$X = 1 - \exp\{-k[a/R]t\}$$

where:

k is a rate constant which is a function of temperature;

[alR] is the molar concentration of aluminum alkyl;

t is reaction time in hours; and

X is vinyl olefin conversion as defined by the expression:

$$1-[Vi]/[Vi]_o$$

where:

[Vi] is the vinyl olefin molar concentration at time t; and

[Vi]$_o$ is the initial vinyl olefin molar concentration.

Values for the rate constant, k, are in terms of liters per gram mol per hour.

The vinyl olefins used in the process can be one or more linear vinyl olefins or one or more branched chain vinyl olefins or any mixture of these. Minor amounts of internal and/or vinylidene monoolefins (e.g., up to 40 mol % of an olefin mixture) can be present in the initial vinyl olefin charged to the reactor. The amount of such internal and/or vinylidene olefins, if any, is of course excluded from consideration when calculating the mol ratios of catalyst to initial vinyl olefin used in the process. Typically the vinyl olefins used in the process will contain in the range of about 3 to about 30 or more carbon atoms per molecule. Preferably the initial vinyl olefin will contain in the range of 4 to 20, and still more preferably in the range of 8 to 16 carbon atoms per molecule. For some end use applications, it is desirable to use a substantially pure single vinyl olefin, such as 1-butene, 1-pentene, 1-hexene, 1-octene, 1-decene, or 1-tetradecene. For other end use applications mixtures of vinyl olefins are entirely suitable. In such case co-dimerization (a special case of dimerization) takes place.

Any trialkylaluminum compound can used as the sole catalytic component charged to the dimerization reaction zone in the practice of this invention. Typically the alkyl groups will contain from 1 to 30 carbon atoms, and preferably in the range of 2 to about 18 carbon atoms each. Most preferred are trialkylaluminum compounds in which substantially all of the alkyl groups are a straight chain primary alkyl groups having in the range of from 2 to about 14 carbon atoms, such as triethylaluminum, tripropylaluminum, tributylaluminum, trihexylaluminum, trioctylaluminum, tris(decyl)aluminum, tris(tetradecyl) aluminum, and the like. Mixtures of aluminum trialkyls can be also used if desired. The hydride content, if any, of the aluminum trialkyl should be quite low, e.g., the aluminum trialkyl should have a maximum aluminum hydride equivalent of not more than about 0.8% In preferred embodiments the aluminum trialkyl as fed to the process is essentially hydride-free, i.e., the trialkylaluminum product contains, if any, a maximum of 0.10 wt % of aluminum hydride equivalent, and more preferably a maximum of 0.05 wt % of aluminum hydride equivalent, because the aluminum hydride bond can cause isomerization of 1-olefins to internal olefins.

It is preferred to conduct the process using in the range of about 0.005 to about 0.045 mol of trialkylaluminum per mol of the initial vinyl olefin, and even more preferably about 0.010 to about 0.045 mol of trialkylaluminum per mol of the initial vinyl olefin.

Preferably the dimerization is conducted predominately (more than half of the reaction period) at temperatures in the range of 145° to 170° C. and more preferably predominately in the range of 160° to 170° C. with reaction periods in the range of 1 to 15 hours (preferably in the range of about 6 to about 15 hours) sufficient to convert at least 80% by weight of the initial vinyl olefin to a different product with at least 80 wt % vinylidene dimer selectivity. A particularly preferred embodiment involves conducting the dimerization predominately at temperatures in the range of about 165°±3° C. with reaction periods in the range of about 6 to about 12 hours sufficient to convert at least 85% by weight of the initial vinyl olefin to a different product with at least 80 wt % vinylidene dimer selectivity.

Another feature of this invention is that although aluminum to hydrogen bonds serve as catalysts for isomerization of a 1-olefin to an internal olefin, and although the rate at which trialkylaluminum compounds dissociate into olefin and dialkylaluminum hydride rapidly increases with increasing temperature, the process of this invention enables the formation of vinylidene olefin products of almost as high a purity as the process of U.S. Pat. No. 4,973,788 in much shorter reaction periods.

The reaction should be conducted in an environment that is essentially anhydrous and substantially free of oxygen and air. Aluminum trialkyls can react violently with water or compounds containing hydroxyl groups such as alcohols. Thus even a small amount of water, alcohol, or the like, in the system will inactivate some of the aluminum trialkyl. If it known that some water is present in the vinyl olefin, by use of analysis such as Karl Fischer water analysis, the amount of aluminum alkyl catalyst can be increased to compensate for the water or other active hydrogen component such as alcohol whereby the proper amount of active aluminum trialkyl catalyst remains in the system even after part of the initial aluminum alkyl has been destroyed by the water or other active hydrogen compound. Alternatively, the olefin feed can be pretreated to remove water or alcohol contamination. Likewise the process should be conducted under a dry inert atmosphere e.g., nitrogen, argon, neon, or the like, to prevent catalyst destruction.

It is desirable to have good mixing in the reactor to ensure uniform temperature. In order to avoid high reactor skin temperature, it is desirable to set the temperature of the reactor heating medium at (or close to) the desired reaction temperature. Both heat from the heating medium and heat of reaction are utilized to bring the reaction mixture from room temperature to the reaction temperature. When the reactor temperature is higher than the temperature of the heating medium, the heat transfer direction will be reversed, i.e., from reaction mixture to the heating medium. Thus, the same heating medium at almost the same temperature may be used both as the heating medium during heat up to reaction temperature, and, as the cooling medium if and when the reaction temperature is passed. Either steam or other heating media such as Dowtherm may be used.

With a jacketed 30 gallon glass-lined Pfaudler batch reactor having a heat transfer area:reactor volume ratio of 2.4 ft$^2$:ft$^3$, passage of 110 psig steam through the jacket to control reaction temperature in the range of 165°–170° C. has proven very satisfactory in actual practice.

The preferred material of construction at least for the interior of dimerization reactor is either carbon steel, glass-lining, or mild metals such as copper. Nickel is known to isomerize vinyl olefins to internal olefins. Thus, materials which contain Ni such as stainless steel, alloy 20, Inconel, etc., are preferably avoided. Also, Ni-containing feed and transfer lines should be avoided whenever possible. Reactors made with materials such as stainless steel may become passivated after a few cycles of operation to increase dimer yield. Commonly owned copending application Ser. No. 08/598,801 (Case OL-6962), filed Feb. 5, 1996

(contemporaneously herewith) by K. F. Lin describes a process in which passivation of ferrous metal surfaces including substantially-nickel free steels and nickel-free steels can be accomplished, and this procedure may be utilized in the practice of this invention. The procedure involves passivation of the surface with air or oxygen. Commonly owned copending application Ser. No. 08/596, 812 (Case OL-6963), filed Feb. 5, 1996 (contemporaneously herewith) by D. H. Krzystowczyk and K. F. Lin describes use of acetylenic hydrocarbons for overcoming the devastating effect of nickel on dimer selectivity in a process wherein a vinyl olefin is dimerized by use of an aluminum alkyl catalyst. The entire disclosures of these copending applications are incorporated herein by reference as if fully set forth herein.

Metal impurities in or on surfaces that contact the reactor feed or contents such as Na, Li, etc. may also enhance isomerization of vinyl olefins and should also be avoided wherever possible.

Thus there are a number of things that should be done in order to achieve the optimum results achievable by the practice of this invention, especially when using reaction equipment that has been used previously for conducting other kinds of chemical reactions. Such matters are considered below.

Prior to feed transfer to the dimerization reactor, the reactor should be cleaned with aqueous and/or organic solvents. The pre-reaction cleanup procedures may include some of the following steps: A) Caustic or acidic wash; B) Water wash; C) Drying (removal of water); D) Heptane (or other heavy paraffin/olefin) wash; and E) Drying (removal of heptane or other heavy paraffin/olefin.) Caustic or acidic washing may introduce trace amount of impurities either from the solution or from leaching of material from the interior reactor surfaces. Therefore it is desirable to avoid use of caustic or acidic washing of reactor surfaces. In cases where hot organic solvent wash alone is sufficient to clean up the reactor, aqueous wash is not needed. But in cases where aqueous wash is needed to accomplish the reactor cleanup, use of steam cleaning or hot water wash without use of base or acid is preferred. Caustic or acidic wash should only be used if the other alternatives are inadequate in any given situation.

If the reactor history is such that caustic or acidic wash is needed, this should be followed with fresh water washes several times until the quality of final washed water is the same as (or close to) the fresh water used. This may be accomplished by measuring pH or ionic strength (such as Ni, Na, Cl, etc.). Since trace amounts of isomerization promoters can reduce dimer yield tremendously, the purest water available at the plant site (e.g., deionized water or distilled water) is preferably used. After water wash is complete and the final wash water is discharged, the reactor should be blown to dryness with by nitrogen, as any residual water in the reactor will destroy the corresponding amount of aluminum alkyl catalyst. After aqueous wash of the reactor, organic solvent wash (heptane or others) should follow. Hot heptane wash for several hours under agitation conditions can expedite the organic wash process. After heptane wash and discharge of waste heptane, the reactor is preferably purged with nitrogen to dry the reactor. Nitrogen purge with some heat in the reactor accelerates the heptane drying process. If the reaction vessel(s) and/or transfer lines or other auxiliaries that contact the feeds or reaction mixture are composed of nickel-containing steel alloys or other ferrous metal surfaces so that passivation of the contacting surface(s) should be carried out, and if the passivation is to be effected by use of air (or oxygen) rather than by another method such as use of an aliphatic acetylenic hydrocarbon, the cleaned reactor and associated metallic equipment with which the feeds and reaction mixtures come in contact are exposed to air for at least 0.5 hour, preferably for from 0.5 to 3 hours at a temperature of at least about 20° C., such as ambient room temperature up to about 50° C. Shorter exposure periods can be used when employing pure oxygen for surface passivation.

After all of the heptane (or other heavy paraffin/olefin) is removed and the steel surfaces passified by contact with air or oxygen (if this particular method of passivation has been selected), the dimerization reactor should be maintained with 10 psig $N_2$ at room temperature. All further processing is performed under a blanket of dry inert gas, preferably a nitrogen blanket.

Whenever possible, the feed transfer lines should be treated with the same diligence as the reactor pretreatment procedure to ensure that no contamination of feeds occurs from the transfer lines.

After the dimerization reactor and associated feed transfer lines have been cleaned up, it is desirable to conduct a blank isomerization operation. This involves charging the reactor under a $N_2$ blanket or purge with vinyl olefin feed of the type to be used for dimerization. In the absence of trialkylaluminum catalyst, the olefin feed is then heated to 165° C. and kept at that temperature for about 12 hours. Such a blank isomerization test makes it possible to determine if there is any isomerization activity in the system in the absence of the trialkylaluminum catalyst. Pilot plant experience has indicated that there is no isomerization in the above glass-lined reactor during the blank isomerization test.

If heavy olefin such as tetradecene is used in the reactor pretreatment, a blank isomerization test can be also carried out with the hot heavy olefin during the reactor cleanup.

The reactor must pass a blank isomerization test before proceeding to dimerization. If it does not, the reactor can be cooked for another 24–48 hours using the same olefin to remove any residual materials which may not be completely removed during the reactor pretreatment. Also, if the reactor or portions of the reaction system that contact the feeds and/or reaction mixture are nickel-containing steel alloys, another passivation treatment at this stage may be necessary or desirable. Then another blank isomerization test should be conducted using another fresh charge of the olefin feed. If this blank isomerization test still fails, further investigation is required to determine the cause. In this connection, failure in a blank isomerization test is deemed to be the formation in the olefin of 0.5% by weight or more of internal olefin as determined by NMR.

After achieving a satisfactory blank isomerization test, the specified amount of trialkylaluminum is charged and mixed with the vinyl olefin in the reactor containing 90 wt % of the specified total amount olefin feed to be used in the reaction. Then the remaining amount of vinyl olefin (10 wt % of specified total olefin feed) is charged to flush out any trialkylaluminum which may be trapped in the feed transfer line.

A preferred series of process steps includes: A) Batch dimerization; B) Caustic wash; C) Phase separation; and D) Distillation. These steps are briefly discussed below.

Batch dimerization is most preferably carried out at 165° C. using substantially pure linear alpha-olefin (LAO) as the vinyl olefin feed and a charge of triethylaluminum (TEA) as the catalyst. At a TEA/LAO feed molar ratio of 0.0167, reaction under these conditions typically achieves 90% LAO conversion in 12 hours reaction time. During the dimerization of an alpha-olefin (e.g., 1-octene), TEA will be converted at least in part to trialkylaluminum in which the alkyl groups correspond to the alpha-olefin (in this example, to tri-n-octyl aluminum).

In conducting the dimerization reactions of this invention it is desirable to have a low volume of vapor space to minimize isomerization in the vapor phase which in turn can reduce selectivity to dimer formation. In general the vapor space or free space in the reactor will fall in the range of 0 to 40%. Preferably, the feed charge is such that at reaction temperature (e.g., 165° C.), the liquid phase occupies at least 70%, more preferably over 80%, still more preferably 90% or more, and most preferably at least about 95% or more, of the internal reactor volume.

The catalyst can be, and preferably is, recovered from the reaction product and recycled to the dimerization reactor.

The following Examples illustrate the results that can be achieved by the practice of this invention. As indicated, these Examples are intended to illustrate, and should be understood to illustrate, and not limit this invention. All reactions in these Examples reactions were conducted in a stirred 30-gallon glass-lined Pfaudler reactor.

EXAMPLES 1 AND 2

Several reactions were conducted in which 1-octene was dimerized using tri-n-octylaluminum as the catalyst. In Examples 1 and 2 the reactions were performed pursuant to this invention using a dimerization temperature of 165° C. and short reaction periods. The results are summarized in Table 1. For comparative purposes Table 1 also shows the same type of information from Example 6 of U.S. Pat. No. 4,973,788 ("Pat. 6") wherein 1-octene was dimerized using tri-n-octylaluminum as catalyst, but not under the conditions of this invention. Also shown in Table 1 for comparative purposes is a run ("Comp. A") in which 1-octene was dimerized using tri-n-octylaluminum as catalyst but at 120° C. In each case, catalyst concentration is expressed in terms of mols of tri-n-octylaluminum ("TNOA") per mol of initial 1-octene. The values given for deep internal dimer also include small amounts of deep internal monomer. The times given in Table 1 are the times required to reach 90% conversion of vinyl olefin under the reaction conditions used.

TABLE 1

| Example | TNOA Conc. | Time, hrs. | β-Internal Monomer, wt % | Deep Int. Dimer, wt % | Vinylidene Dimer, wt % |
| --- | --- | --- | --- | --- | --- |
| 1 | 0.043 | 5 | 6.6 | 9.6 | 83.8 |
| 2 | 0.0054 | 45 | 5.4 | 7.3 | 87.3 |
| Pat. 6 | 0.043 | 5 | 15 | 14 | 71 |
| Comp. A | 0.017 | 183 | 2.0 | 5.6 | 92.3 |

EXAMPLES 3 AND 4

Dimerizations of 1-octene were conducted in the same reactor as in Examples 1 and 2, but using triethylaluminum as the catalyst charged to the reactor. The triethylaluminum catalyst of Example 3 was a commercial product with a specification for aluminum hydride equivalent of 0.8 wt % maximum. In Example 4, the product specification for aluminum hydride equivalent was 0.10 wt % maximum. Other reaction conditions and results are summarized in Table 2. Triethylaluminum ("TEA") concentration is given as mols of TEA per mol of 1-octene fed to the reactor.

TABLE 2

| Conditions Used | Example 3 | Example 4 |
| --- | --- | --- |
| TEA Concentration | 0.012 | 0.017 |
| Reaction Temperature, °C. | 165 | 165–170 |
| Reaction Time, hours | 19 | 15 |
| 1-Octene Conversion, % | 92 | 95 |
| Hours to Reach 90% Conversion | 17 | 12 |
| Dimer Selectivity, wt % | 91 | 90 |
| Vinylidene Purity, wt % | 93 | 92 |

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for producing vinylidene olefin using a trialkylaluminum compound as the sole catalyst component charged to the reaction vessel, which process comprises dimerizing vinyl olefin with at least one trialkylaluminum compound as the catalyst in a ratio in the range of 0.001 to 0.05 mol of trialkylaluminum per mol of the initial vinyl olefin at a temperature in the range of over 140° and below 172° C. for a period of time in the range of 1 to 24 hours sufficient to convert at least 10% by weight of the initial vinyl olefin to a different product with at least 80 wt % vinylidene dimer selectivity.

2. A process of claim 1 wherein the trialkylaluminum as charged to the reaction vessel is one or more trialkylaluminum compounds in which substantially all of the alkyl groups are straight chain primary alkyl groups having in the range of from 2 to about 14 carbon atoms.

3. A process of claim 1 wherein the trialkylaluminum as charged to the reaction vessel contains, if any, a maximum of 0.10 wt % of aluminum hydride equivalent.

4. A process of claim 1 wherein the trialkylaluminum as charged to the reaction vessel is triethylaluminum.

5. A process of claim 4 wherein the triethylaluminum as charged to the reaction vessel contains, if any, a maximum of 0.10 wt % of aluminum hydride equivalent.

6. A process of claim 1 wherein the vinyl olefin charged to the reactor contains in the range of 3 to 20 carbon atoms per molecule.

7. A process of claim 6 wherein said vinyl olefin is a single vinyl olefin.

8. A process of claim 6 wherein said vinyl olefin is a mixture of two or more vinyl olefins.

9. A process of claim 1 wherein said ratio is in the range of about 0.005 to about 0.045 mol of trialkylaluminum per mol of the initial vinyl olefin.

10. A process of claim 1 wherein said ratio is in the range of about 0.010 to about 0.045 mol of trialkylaluminum per mol of the initial vinyl olefin.

11. A process of claim 1 wherein the dimerization is conducted predominately at temperatures in the range of 160° to 170° C. with reaction periods in the range of 1 to 15 hours sufficient to convert at least 80% by weight of the initial vinyl olefin to a different product.

12. A process of claim 1 wherein the dimerization is conducted predominately at temperatures in the range of about 165°±3° C. with reaction periods in the range of about 6 to about 12 hours sufficient to convert at least 85% by weight of the initial vinyl olefin to a different product.

13. A process of claim 1 wherein the vinyl olefin charged to the reactor contains in the range of 6 to 20 carbon atoms per molecule, wherein the trialkylaluminum as charged to the reaction vessel is one or more trialkylaluminum compounds in which substantially all of the alkyl groups are straight chain primary alkyl groups having in the range of from 2 to about 20 carbon atoms, and wherein the trialkylaluminum as charged to the reaction vessel contains, if any, a maximum of 0.10 wt % of aluminum hydride equivalent.

14. A process of claim 13 wherein said ratio is in the range of about 0.005 to about 0.045 mol of trialkylaluminum per mol of the initial vinyl olefin, and wherein the dimerization is conducted predominately at temperatures in the range of 160° to 170° C. with reaction periods in the range of 1 to 15 hours sufficient to convert at least 80% by weight of the initial vinyl olefin to a different product.

15. A process of claim 14 wherein the trialkylaluminum as charged to the reaction vessel is triethylaluminum.

16. A process of claim 15 wherein the triethylaluminum as charged to the reaction vessel contains, if any, a maximum of 0.10 wt % of aluminum hydride equivalent.

17. A process of claim 1 wherein the vinyl olefin charged to the reactor contains in the range of 4 to 16 carbon atoms per molecule and wherein said ratio is in the range of about 0.010 to about 0.045 mol of trialkylaluminum per mol of the initial vinyl olefin.

18. A process of dimerizing vinyl olefin to produce vinylidene olefin which comprises:
a) introducing into a reactor (i) vinyl olefin to be dimerized and (ii) a trialkylaluminum compound as the sole catalyst component charged to the reactor, (i) and (ii) being proportioned to result in a ratio in the range of 0.001 to 0.05 mol of trialkylaluminum per mol of the initial vinyl olefin, thereby forming a reaction mixture;
b) maintaining the reaction mixture under a substantially anhydrous oxygen-free conditions and at a temperature in the range of 145° to 170° C. for a period of time in the range of 1 to 24 hours sufficient to convert at least 10% by weight of the initial vinyl olefin to a different product with at least 80 wt % vinylidene dimer selectivity.

19. A process of claim 1 wherein the process is conducted such that the relationship among vinyl olefin conversion, reaction time and catalyst concentration is in accordance with the expression:

$$X=1-\exp\{-k[alR]t\}$$

where:

k is the rate constant in terms of liters per gram mol per hour;

[alR] is the molar concentration of aluminum alkyl;

t is reaction time in hours; and

X is vinyl olefin conversion as defined by the expression:

$$1-[Vi]/[Vi]_o$$

where:

[Vi] is the vinyl olefin molar concentration at time t; and

[Vi]$_o$ is the initial vinyl olefin molar concentration.

20. A process of claim 18 wherein the process is conducted such that the relationship among vinyl olefin conversion, reaction time and catalyst concentration is in accordance with the expression:

$$X=1-\exp\{-k[alR]t\}$$

where:

k is the rate constant in terms of liters per gram mol per hour;

[alR] is the molar concentration of aluminum alkyl;

t is reaction time in hours; and

X is vinyl olefin conversion as defined by the expression:

$$1-[Vi]/[Vi]_o$$

where:

[Vi] is the vinyl olefin molar concentration at time t; and

[Vi]$_o$ is the initial vinyl olefin molar concentration.

21. A process of claim 20 wherein the trialkylaluminum as charged to the reaction vessel is triethylaluminum containing, if any, a maximum of 0.10 wt % of aluminum hydride equivalent.

* * * * *

UNITED STATES PATENT AND TRADEMARK OFFICE
CERTIFICATE OF CORRECTION

PATENT NO.: 5,625,105

DATED: April 29, 1997

INVENTOR(S): Kaung-Far Lin, Carroll W. Lanier

It is certified that error appears in the above-identified patent and that said Letters Patent is hereby corrected as shown below:

| Col. | Line | |
|---|---|---|
| 3 | 35 | "Any trialkylaluminum compound can used" should read --Any trialkylaluminum compound can be used-- |
| 4 | 24-25 | "If it known that some water is present" should read --If it is known that some water is present-- |
| 5 | 32-33 | "Caustic or acidic washing may introduce trace amount of impurities" should read --Caustic or acidic washing may introduce trace amounts of impurities-- |
| 5 | 53-54 | "the reactor should be blown to dryness with by nitrogen," should read --the reactor should be blown to dryness with nitrogen,-- |

Signed and Sealed this

Twelfth Day of August, 1997

Attest:

BRUCE LEHMAN

*Attesting Officer*    *Commissioner of Patents and Trademarks*